United States Patent [19]
Jameel et al.

[11] Patent Number: 5,584,856
[45] Date of Patent: Dec. 17, 1996

[54] REMOVABLE SURGICAL STAPLE

[76] Inventors: Irfan M. Jameel, 1895 Old Clinton Rd., Apt. A-14, Macon, Ga. 31211; Joe S. Robinson, Jr., 562 College St., Macon, Ga. 31201

[21] Appl. No.: 360,643

[22] Filed: Dec. 21, 1994

[51] Int. Cl.$^6$ .................................................. A61B 17/04
[52] U.S. Cl. .................. 606/220; 606/215; 606/216; 606/218; 606/217
[58] Field of Search .................... 606/215, 216, 606/217, 218, 219, 220; 411/457

[56] References Cited

U.S. PATENT DOCUMENTS

| | | | |
|---|---|---|---|
| 19,747 | 3/1858 | Boardman . | |
| 262,635 | 8/1882 | Adams . | |
| 356,202 | 1/1887 | Kempshall . | |
| 2,058,020 | 5/1935 | Jaffe | 24/90 |
| 3,515,194 | 3/1969 | Hirst | 151/41.72 |
| 4,060,089 | 11/1977 | Noiles | 606/220 |
| 4,454,875 | 6/1984 | Pratt et al. | 128/92 |
| 4,534,350 | 8/1985 | Golden et al. | 128/334 |
| 4,610,250 | 9/1986 | Green | 128/334 |
| 4,946,458 | 8/1990 | Harms et al. | 606/72 |
| 5,258,011 | 11/1993 | Drews | 606/220 |

*Primary Examiner*—Gary Jackson
*Attorney, Agent, or Firm*—Kennedy & Kennedy

[57] ABSTRACT

A surgical staple (10) is provided having a fastener member (11) and a retainer member (12). The retainer member has an internal channel (31) having ridges (33) with serrated teeth (35). The fastener member has a tubular head (13), and a series of prongs (14) removably mounted to the tubular head by a locking pin (15). The prongs have two flexible arms (23) with serrated teeth (24) adapted to mate with the serrated teeth of the retainer member to lock the fastener member to the retainer member.

22 Claims, 1 Drawing Sheet

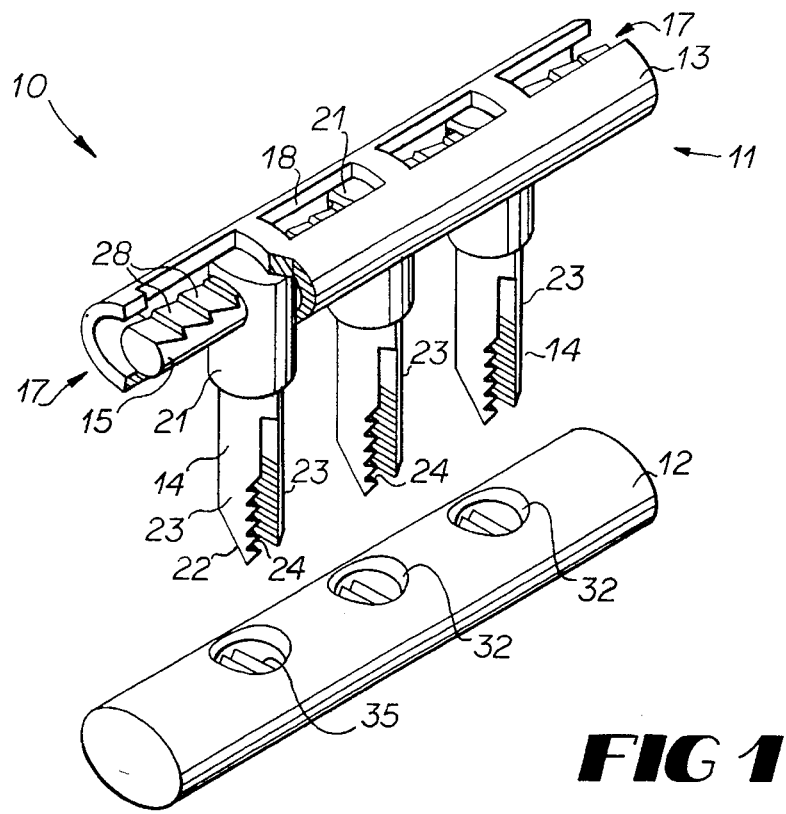
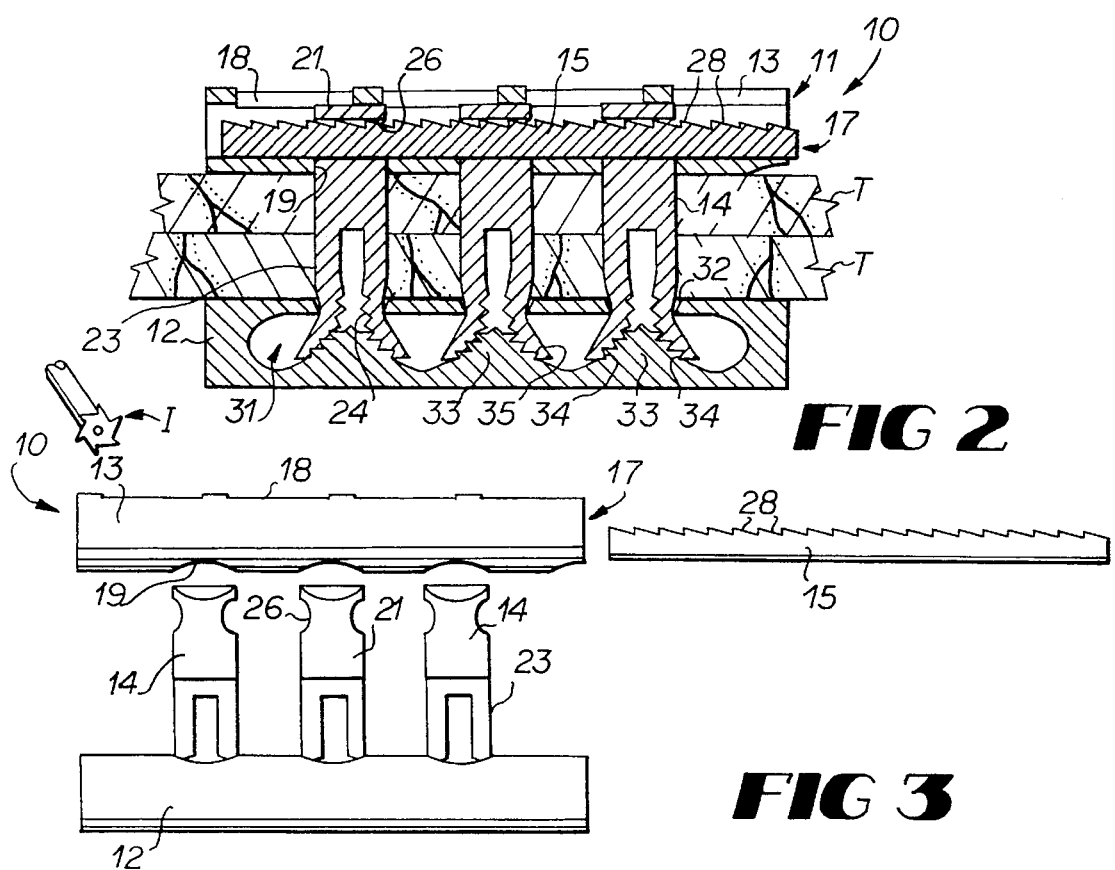

REMOVABLE SURGICAL STAPLE

TECHNICAL FIELD

This invention relates to surgical staples used to hold together in vivo tissue, and especially to surgical staples which are removed.

BACKGROUND OF THE INVENTION

Surgical staples allow a surgeon to hold together body tissue. Staples may be applied singularly or in a series depending upon the length of tissue to be held together. Some staples are designed to be applied to the surface of skin. These types of staples are easily accessible and removable. Staples have also been designed to hold internal tissues. These staples are often made of inert metals which are stapled within the body or of dissolvable materials such as magnesium or non-metallic resinous material which are gradually absorbed by the body.

Metal staples are typically bent or crimped to hold the tissue to which they are applied. These staples however are difficult to uncrimp and remove. Metallic staples also cause X-rays to scatter causing a degradation of the resulting X-ray photograph.

Resinous materials are typically resilient which prevents them from being crimped. Hence, these types of staples are typically comprised of a fastener member with two prongs and a retainer member, as shown in U.S. Pat. No. 4,534,350. The prongs of the fastener member are driven into one side of the tissue to be held and the retainer member interlocks with the prongs protruding from the other side of the tissue to hold the staple in place. Once the fastener is interlocked however it cannot be unlocked. Therefore, should the tissue not be properly stapled it must undergo a revision wherein the stapled portion of the tissue is cut and removed and then restapled. This obviously causes additional damage to the tissue and lengthens the time of the surgical procedure.

Accordingly, it is seen that a need remains for a surgical staple which may be easily removed. It is to the provision of such therefore that the present invention is primarily directed.

SUMMARY OF THE INVENTION

In a preferred form of the invention a surgical staple for holding together tissue in vivo comprises at least one prong having a mounting end and a tissue piercing end. The surgical staple also has a head removably mounted to the mounting end of the prong, and a retainer adapted to receive and retain the piercing end of the prong with the head and retainer overlying the tissue and with the prong piercing the tissue.

BRIEF DESCRIPTION OF THE DRAWING

FIG. 1 is a perspective view of a surgical staple embodying principles of the invention is a preferred form.

FIG. 2 is a cross-sectional view of the surgical staple of FIG. 1.

FIG. 3 is a front view of the surgical staple of FIG. 1 shown with a head portion removed from prongs.

DETAILED DESCRIPTION

With reference next to the drawings, there is shown a surgical staple 10 having a fastener member 11 and a retainer member 12 both made of either non-biodegradable material such as metal or biodegradable material such as resinous material. The fastener member 11 has a tubular head 13, three removable prongs 14 and a removable locking pin 15 extending through the prongs 14. The tubular head 13 has open ends 17, a series of slots 18 extending into the tubular head 13 and a series of holes 19 extending into the tubular head 13 opposite the slots 18. Each prong 14 has a head portion 21 and a piercing tip 22 having two flexible arms 23 with inwardly facing serrated teeth 24. The head portions 21 of prongs 14 have a hole 26 therethrough sized and shaped to receive locking pins 15. The locking pins 15 have serrated teeth 28 extending along their entire length. As best shown in FIG. 2, the retainer member 12 has an internal channel 31 and three passages 32 extending to the internal channel 31. Internal channel 31 has three inverted, V-shaped ridges 33, each aligned with a passage 32. Ridges 33 are defined by diverging slopes 34 having serrated teeth 35 thereon sized and shaped to mate with the serrated teeth 24 of the prong flexible arms 23.

In use, the fastener member 11 is positioned on one side of tissue T to be held with the prongs 14 oriented at an appropriate angle to penetrate the tissue. The retainer member 12 is held on the other side of the tissue T opposite the fastener member 11 with the retainer member passages 32 aligned with the prongs 14. The fastener member 11 and retainer member 12 are brought together thereby forcing the prongs 14 through the tissue T and into the passages 32 of the retainer member. Continued movement of the prongs 14 into the retainer member passages 32 causes the flexible arms 23 to diverge along opposite slopes 34 of ridges 33 whereby the teeth 24 of the arms interlock with the teeth 35 of the ridges, as shown in FIG. 2. The interlocking of teeth 24 and 35 locks the fastener member 11 with the retainer member 12. Relative movement between the fastener member and the retainer member is terminated when the fastener member is positioned an appropriate distance from the retainer member to hold the tissue T securely therebetween.

The above described method for applying the surgical staple 10 to the tissue may be effected with a conventional instrument designed to hold the fastener member and retainer member and to urge the prongs through the tissue and into the retainer member.

The staple 10 is removed by inserting an instrument I into the slot 18 of the fastener member 11 so as to contact the serrated teeth 28 of the locking pin 15. The instrument for doing such may be a motor driven wheel having teeth sized and shaped to mate with locking pin teeth 28 or simply an elongated probe. These instruments drive the locking pin 15 from within the hole 26 of the prong head portion 21 through the open end 17 of head 13, thereby allowing the prongs 14 to be released from the tubular head 13, as shown in FIG. 3. The prongs 14 are then passed through the tissue in the same direction in which they were inserted. The tubular head 13, locking pin 15 and retainer member 12 with prongs 14 mounted thereto are removed from the body.

It thus is seen that a surgical staple is now provided which may be removed without having to sever the prongs of the staple. It should be understood that the number of prongs may be varied according to the size of the tissue to be held. As such, the staple may be provided with as little as one prong.

While this invention has been described in detail with particular references to the preferred embodiment thereof, it should be understood that many modifications, additions and deletions, in addition to those expressly recited, may be made thereto without departure from the spirit and scope of the invention as set forth in the following claims.

We claim:

1. A surgical staple for holding together tissue in vivo comprising at least one prong having a mounting end and a tissue piercing end, a head removably mounted to said mounting end of said prong, and a retainer adapted to receive and retain said piercing end of said prong with said head and retainer overlying the tissue and with said prong piercing the tissue.

2. The surgical staple of claim 1 wherein said mounting end of said prong has a hole therein and wherein said head comprises a tubular member adapted to receive said mounting end of said prong and a lock pin sized and shaped to be received within said hole of said prong mounting end mounted within said tubular member.

3. The surgical staple of claim 2 wherein said lock pin has serrated teeth along its longitudinal axis and said tubular member has a channel aligned with said serrated lock pin whereby the serrated teeth of said lock pin are accessible from the exterior of the tubular member.

4. The surgical staple of claim 1 wherein said prong has serrated teeth and said retainer has serrated teeth adapted to mate with said teeth of said prong.

5. The surgical staple of claim 4 wherein said prong has two flexible members each having serrated teeth.

6. The surgical staple of claim 5 wherein said serrated teeth of said flexible members face each other and said retainer includes a tubular member having a hole extending therein and a ridge upon which extends said retainer serrated teeth, said ridge being aligned with said tubular member hole in a position to extend between said flexible members extending through said tubular member hole.

7. The surgical staple of claim 4 wherein said mounting end of said prong has a hole therein and wherein said head comprises a tubular member adapted to receive said mounting end of said prong and a lock pin sized and shaped to be received within said hole of said prong mounting end mounted within said tubular member.

8. The surgical staple of claim 7 wherein said lock pin has serrated teeth along its longitudinal axis and said tubular member has a channel aligned with said serrated lock pin whereby the serrated teeth of said lock pin are accessible from the exterior of the tubular member.

9. The surgical staple of claim 1 wherein said head is mountable to a plurality of prongs and said retainer is adapted to receive a plurality of prongs.

10. The surgical staple of claim 1 wherein said prong, said head and said retainer are made of a biodegradable material.

11. The surgical staple of claim 1 wherein said prong, said head and said retainer are made of a non-biodegradable material.

12. A surgical staple for holding together tissue in vivo comprising a prong having a shaft with a tissue piercing tip, a head removably mounted to an end of said shaft opposite said shaft piercing tip, and a retainer adapted to be coupled to said piercing tip of said prong shaft, whereby the surgical staple holds tissue between the head and the retainer by securing the prong to the retainer and the head of the prong may be removed to allow the shaft to be passed through the tissue and thereby release the tissue.

13. The surgical staple of claim 12 wherein said mounting end of said prong has a hole therein and wherein said head comprises a tubular member adapted to receive said mounting end of said prong and a lock pin sized and shaped to be received within said hole of said prong mounting end mounted within said tubular member.

14. The surgical staple of claim 13 wherein said lock pin has serrated teeth along its longitudinal axis and said tubular member has a channel aligned with said serrated lock pin whereby the serrated teeth of said lock pin are accessible from the exterior of the tubular member.

15. The surgical staple of claim 12 wherein said prong has serrated teeth and said retainer has serrated teeth adapted to mate with said teeth of said prong.

16. The surgical staple of claim 15 wherein said prong has two flexible members each having serrated teeth.

17. The surgical staple of claim 16 wherein said serrated teeth of said flexible members face each other and said retainer includes a tubular member having a hole extending therein and a ridge upon which extends said retainer serrated teeth, said ridge being aligned with said tubular member hole in a position to extend between said flexible members extending through said tubular member hole.

18. The surgical staple of claim 15 wherein said mounting end of said prong has a hole therein and wherein said head comprises a tubular member adapted to receive said mounting end of said prong and a lock pin sized and shaped to be received within said hole of said prong mounting end mounted within said tubular member.

19. The surgical staple of claim 18 wherein said lock pin has serrated teeth along its longitudinal axis and said tubular member has a channel aligned with said serrated lock pin whereby the serrated teeth of said lock pin are accessible from the exterior of the tubular member.

20. The surgical staple of claim 12 wherein said head is mountable to a plurality of prongs and said retainer is adapted to receive a plurality of prongs.

21. The surgical staple of claim 12 wherein said prong, said head and said retainer are made of a biodegradable material.

22. The surgical staple of claim 12 wherein said prong, said head and said retainer are made of a non-biodegradable material.

* * * * *